United States Patent
Oguro

(10) Patent No.: US 8,324,407 B2
(45) Date of Patent: Dec. 4, 2012

(54) ALCOHOL COMPOUND HAVING DIOXANE STRUCTURE AND PROCESS FOR PRODUCING SAME

(75) Inventor: Dai Oguro, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/146,752

(22) PCT Filed: Jan. 28, 2010

(86) PCT No.: PCT/JP2010/051110
§ 371 (c)(1),
(2), (4) Date: Jul. 28, 2011

(87) PCT Pub. No.: WO2010/087394
PCT Pub. Date: Aug. 5, 2010

(65) Prior Publication Data
US 2011/0282076 A1   Nov. 17, 2011

(30) Foreign Application Priority Data
Jan. 30, 2009 (JP) ................... 2009-019591

(51) Int. Cl.
*C07D 319/06* (2006.01)
(52) U.S. Cl. ...................................... 549/374
(58) Field of Classification Search ................ 549/374
See application file for complete search history.

(56) References Cited

U.S. PATENT DOCUMENTS

| | | | |
|---|---|---|---|
| 4,085,222 A | 4/1978 | Rhodes et al. | |
| 4,876,368 A | 10/1989 | Broussard et al. | |
| 5,258,477 A | 11/1993 | Tsai et al. | |

FOREIGN PATENT DOCUMENTS

| | | |
|---|---|---|
| JP | 50 83377 | 7/1975 |
| JP | 60 072884 | 4/1985 |
| JP | 2 19373 | 1/1990 |
| JP | 3 122104 | 5/1991 |
| JP | 2001 031671 | 2/2001 |
| JP | 2001 206882 | 7/2001 |
| PL | 162441 | 12/1993 |
| PL | 163371 | 3/1994 |

OTHER PUBLICATIONS

Hannig, CA Plus Doc. No. 70:115085, 1969.*
Piasecki, CA Plus Doc. No. 123:59616, 1993.*
U.S. Appl. No. 13/143,677, filed Jul. 7, 2011, Minezaki, et al.
U.S. Appl. No. 13/143,612, filed Jul. 7, 2011, Minezaki, et al.
Hannig, E. et al., "Preparation of Some 2-Substituted 5-Ethyl-5-Hydroxymethyl1-1, 3-Dioxanes and Their Carbamic Acid Esters", Pharmazie, vol. 24, No. 1, pp. 32-35, (1969).
Shostakovskii, M. F. et al., Chemistry of Trimethylolethane. II. Vinylation of Trimethylolethane and Some 2, 5-Dialkyl (Alkyl, Aryl)-5-Methylol-1, 3-Dioxanes, Izvestiya Akademii Nauk SSSR, Seriya Khimicheskaya, vol. 1, pp. 133-137, (1966).
International Search Report Issued Mar. 30, 2010 in PCT/JP10/051110 filed Jan. 28, 2010.

* cited by examiner

*Primary Examiner* — Golam M M Shameem
*Assistant Examiner* — Karen Cheng
(74) *Attorney, Agent, or Firm* — Oblon, Spivak, McClelland, Maier & Neustadt, L.L.P.

(57) ABSTRACT

Disclosed is an alcohol compound which is useful as a raw material and an intermediate for paints, adhesives, medicines, cosmetics, food additives, surfactants and the like, further disclosed is a method for producing the above compound.
The above alcohol compound is represented by the following Formula (1):

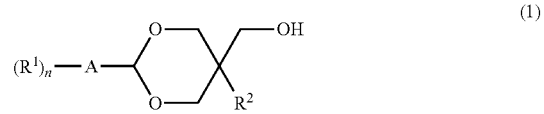

wherein A represents an aromatic ring selected from the group consisting of benzene, naphthalene, anthracene, phenanthrene and pyrene; $R^1$ represents an alkyl group having 1 to 12 carbon atoms, a substituted or unsubstituted aryl group having 6 to 10 carbon atoms or a halogen atom; n represents an integer of 0 to 4; provided that when A is benzene, n represents an integer of 1 to 4; when n represents an integer of 2 to 4, plural $R^1$ may be the same or different from each other; and $R^2$ represents a hydrogen atom, methyl or ethyl.

8 Claims, No Drawings

ALCOHOL COMPOUND HAVING DIOXANE STRUCTURE AND PROCESS FOR PRODUCING SAME

This application is a 371 of PCT/JP10/051110 filed Jan. 28, 2010.

TECHNICAL FIELD

The present invention relates to an alcohol compound having a dioxane structure and a method for producing the same, particularly to a cyclic alcohol compound useful as a raw material and an intermediate for paints, adhesives, medicines, cosmetics, food additives, surfactants and the like and a method for producing the above compound.

BACKGROUND ART

Alcohol compounds having a dioxane structure are known as intermediates for cyclic acrylic esters which are raw materials for paints, adhesives and the like. Patent document 1 discloses cyclic alcohol compounds obtained by reaction of benzaldehyde with trimethylolpropane, as intermediates for cyclic acrylic esters.

CITATION LIST

Patent Literature

Patent document 1 JP-A-60-72884

SUMMARY OF INVENTION

Technical Problem

The cyclic alcohol compounds obtained by reaction of benzaldehyde with trimethylolpropane, which are described in the patent document 1, are limited in uses thereof in a certain case in terms of a solubility, a reactivity, a heat resistance and the like.

The present invention contemplates to provide a cyclic alcohol compound which is useful as a raw material and an intermediate for paints, adhesives, medicines, cosmetics, food additives, surfactants and the like, and to provide a method for producing the above compound.

Solution to Problem

The present invention provides an alcohol compound represented by the following Formula (1):

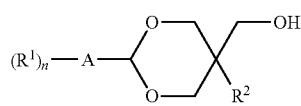

wherein A represents an aromatic ring selected from the group consisting of benzene, naphthalene, anthracene, phenanthrene and pyrene; $R^1$ represents an alkyl group having 1 to 12 carbon atoms, a substituted or unsubstituted aryl group having 6 to 10 carbon atoms or a halogen atom; n represents an integer of 0 to 4; provided that when A is benzene, n represents an integer of 1 to 4; when n represents an integer of 2 to 4, plural $R^1$ may be the same or different from each other; and $R^2$ represents a hydrogen atom, methyl or ethyl.

Advantageous Effects of Invention

The alcohol compound of the present invention can suitably be used as a raw material and an intermediate for paints, adhesives, medicines, cosmetics, food additives, surfactants and the like. In particular, medicines, cosmetics, food additives, surfactants and the like which have a large variety can be produced by using the alcohol compound of the present invention as a raw material or an intermediate therefor.

DESCRIPTION OF EMBODIMENTS

The alcohol compound of the present invention is a compound represented by the following Formula (1):

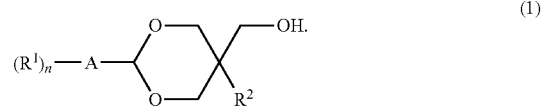

In Formula (1) described above, A represents an aromatic ring selected from the group consisting of benzene, naphthalene, anthracene, phenanthrene and pyrene.

In Formula (1), $R^1$ represents an alkyl group having 1 to 12 carbon atoms, a substituted or unsubstituted aryl group having 6 to 10 carbon atoms or a halogen atom.

The alkyl group in the present invention is a linear, branched or cyclic alkyl group having 1 to 12 carbon atoms, preferably 1 to 9 carbon atoms and more preferably 1 to 4 carbon atoms, and the specific examples thereof include methyl, ethyl, propyl, isopropyl, butyl, isobutyl, t-butyl, cyclohexyl, propylcyclohexyl and the like. The aryl group in the present invention is a substituted or unsubstituted aryl group having 6 to 10 carbon atoms, preferably 6 to 8 carbon atoms, and the specific examples thereof include phenyl, iodophenyl, hydroxyphenyl, dihydroxyphenyl, methoxyhydroxyphenyl, ethoxyhydroxyphenyl and the like. The halogen atom includes a fluorine atom, a chlorine atom, a bromine atom and an iodine atom. $R^1$ is particularly preferably isopropyl or phenyl from the viewpoint of an availability of the raw materials.

In Formula (1) described above, n represents an integer of 0 to 4. Provided that when A is benzene, n represents an integer of 1 to 4. When n represents an integer of 2 to 4, plural $R^1$ may be the same or different from each other, but they are more preferably the same. The term n is preferably 0 or 1 from the viewpoint of an availability of the raw materials.

In Formula (1), $R^2$ represents a hydrogen atom, methyl or ethyl.

The alcohol compound represented by Formula (1) described above is preferably an alcohol compound represented by any of the following Formulae (2) to (4). In Formulae (2) to (4), $R^2$ is the same as $R^2$ in Formula (1) described above, and the preferred ranges thereof are the same.

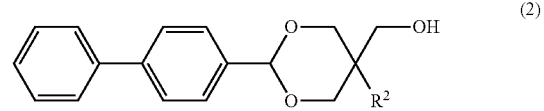

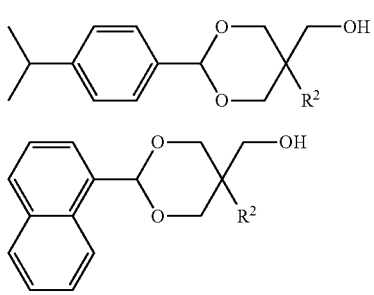

The preferred specific examples of the alcohol compound represented by Formula (1) include 2-(biphenyl-4-yl)-5-ethyl-5-hydroxymethyl-1,3-dioxane, 2-(biphenyl-4-yl)-5-methyl-5-hydroxymethyl-1,3-dioxane, 2-(biphenyl-4-yl)-5-hydroxymethyl-1,3-dioxane, 2-(isopropylphenyl-4-yl)-5-ethyl-5-hydroxymethyl-1,3-dioxane, 2-(1-naphthyl)-5-ethyl-5-hydroxymethyl-1,3-dioxane and the like, but the present invention shall not be restricted to them.

A method for producing the alcohol compound represented by Formula (1) described above shall not specifically be restricted, and it is preferably a method for producing it by reacting 1 mol of aromatic aldehyde represented by the following Formula (A) with 1 to 5 mole, preferably 1 to 2 mol and more preferably 1 to 1.2 mol of trihydric alcohol such as trimethylolmethane, trimethylolethane or trimethylolpropane. Use of the trihydric alcohol makes it possible to notably reduce formation of by-products to enhance the production efficiency.

$(R^1)_n$-A-CHO    (A)

wherein A, $R^1$ and n are the same as A, $R^1$ and n in Formula (1) described above.

In the method for producing the glycol compound according to the present invention, the reaction temperature is preferably 20 to 200° C., more preferably 100 to 180° C. and particularly preferably 120 to 160° C. The targeted compound can efficiently be produced by manufacturing the compound at temperatures falling in the ranges described above.

In the method for producing the alcohol compound according to the present invention, the aromatic aldehyde described above is preferably dropwise added to an organic solvent solution of the trivalent alcohol under the presence of an acid catalyst to react them. This makes it possible to reduce notably formation of by-products and enhance the production efficiency. Further, during the reaction, water contained in the solvent is preferably removed by a Dean-Stark tube and the like.

Acid catalysts such as hydrochloric acid, sulfuric acid, phosphoric acid, paratoluenesulfonic acid, methanesulfonic acid and the like are preferably used as the catalyst which can be used in the present invention, and paratoluenesulfonic acid is particularly preferred. Also, an amount of the acid catalyst used is preferably 0.1 to 30% by mass, particularly preferably 1 to 20% by mass based on the aromatic aldehyde.

The reaction solvent used in the present invention shall not be restricted and is preferably aromatic hydrocarbon base solvents such as benzene, toluene, xylene, mesitylene, anisole and the like; amide base solvents such as dimethylformamide, dimethylacetamide and the like; ether base solvents such as tetrahydrofuran, dioxane, dioxolan and the like; and ester base solvents such as ethyl acetate, butyl acetate and the like. In particular, toluene, dimethylformamide and dimethylacetamide are preferred.

EXAMPLES

The present invention shall be explained below in detail with reference to examples, but the present invention shall not be restricted to the examples shown below.

Example 1

Synthesis of 2-(biphenyl-4-yl)-5-ethyl-5-hydroxymethyl-1,3-dioxane

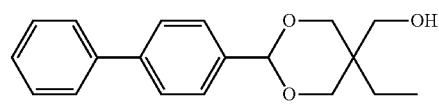

A 5,000 ml flask was charged with 2,000 ml of dimethylacetamide (hereinafter referred to as DMAc, special grade, manufactured by Wako Pure Chemical Industries, Ltd.), 700 ml of toluene (special grade, manufactured by Wako Pure Chemical Industries, Ltd.), 88.8 g (0.74 mol) of trimethylolpropane (special grade, manufactured by Wako Pure Chemical Industries, Ltd.) and 20 g of paratoluenesulfonic acid dihydrate (special grade, manufactured by Wako Pure Chemical Industries, Ltd.), and the mixture was stirred at 100° C. Then, a toluene 700 ml solution of 134 g (0.74 mol) of 4-biphenylaldehyde (special grade, manufactured by Wako Pure Chemical Industries, Ltd.) was dropwise added thereto and heated up to 145° C. A distillate containing water was separated, and the reaction was finished in a reaction time of 5 hours. Water 5 L was put into the reaction liquid, and white crystals were deposited. After filtrated and washed with water, they were concentrated to thereby obtain white crystals (yield: 98%).

The product obtained above was subjected to measurement of a $^1$H-NMR spectrum. An NMR equipment (trade name: R-90H, manufactured by Hitachi, Ltd.) was used for the measurement, and tetramethylsilane (hereinafter referred to as TMS; special grade, manufactured by Wako Pure Chemical Industries, Ltd.) was used as an internal standard substance. The chemical shift values (δ ppm, based on TMS) of $^1$H-NMR of the product obtained in a deuterated dimethylsulfoxide (hereinafter referred to as deuterated DMSO; special grade, manufactured by Wako Pure Chemical Industries, Ltd.) solvent were 0.8-0.9 (t, 3H), 1.6-1.7 (q, 2H), 3.4 (s, 2H), 3.6-3.8 (dd, 4H), 4.7 (s, 1H), 5.5 (s, 1H), 7.3-7.8 (m, 9H).

Example 2

Synthesis of 2-(biphenyl-4-yl)-5-methyl-5-hydroxymethyl-1,3-dioxane

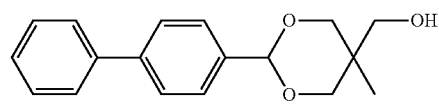

Synthesis and analysis were carried out in the same manners as in Example 1, except that trimethylolpropane was changed to trimethylolethane. The yield was 91%. The chemical shift values (δ ppm, based on TMS) of $^1$H-NMR of the product obtained in the deuterated DMSO solvent were 1.0 (s, 3H), 3.4-3.9 (m, 6H), 4.7 (s, 1H), 5.9 (s, 1H), 7.4-7.5 (m, 9H).

Example 3

Synthesis of 2-(biphenyl-4-yl)-5-hydroxymethyl-1,3-dioxane

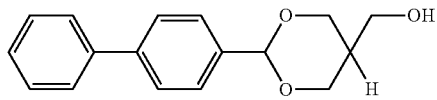

Synthesis and analysis were carried out in the same manners as in Example 1, except that trimethylolpropane was changed to trimethylolmethane. The yield was 89%. The chemical shift values (δ ppm, based on TMS) of $^1$H-NMR of the product obtained in the deuterated DMSO solvent were 1.8 (s, 1H), 3.4-3.9 (m, 6H), 4.7 (s, 1H), 5.9 (s, 1H), 7.4-7.5 (m, 9H).

Example 4

Synthesis of 2-(isopropylphenyl-4-yl)-5-ethyl-5-hydroxymethyl-1,3-dioxane

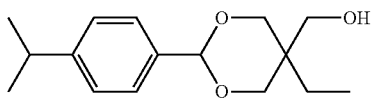

Synthesis and analysis were carried out in the same manners as in Example 1, except that 4-biphenylaldehyde was changed to cuminealdehyde. The yield was 92%. The chemical shift values (δ ppm, based on TMS) of $^1$H-NMR of the product obtained in the deuterated DMSO solvent were 0.9 (t, 3H), 1.2 (d, 6H), 1.7 (q, 2H), 2.9 (m, 1H), 3.4-3.9 (m, 6H), 4.7 (s, 1H), 5.9 (s, 1H), 7.2-7.4 (dd, 4H).

Example 5

Synthesis of 2-(1-naphthyl)-5-ethyl-5-hydroxymethyl-1,3-dioxane

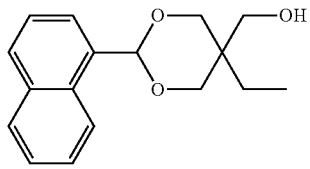

Synthesis and analysis were carried out in the same manners as in Example 1, except that biphenylaldehyde was changed to naphthylaldehyde. The yield was 87%. The chemical shift values (δ ppm, based on TMS) of $^1$H-NMR of the product obtained in the deuterated DMSO solvent were 0.8-0.9 (t, 3H), 1.6-1.7 (q, 2H), 3.4-3.8 (m, 6H), 4.7 (q, 1H), 5.5 (s, 1H), 7.0-8.2 (m, 7H).

INDUSTRIAL APPLICABILITY

The alcohol compound of the present invention can suitably be used as a raw material and an intermediate for paints, adhesives, medicines, cosmetics, food additives, surfactants and the like, and it has a high industrial value. In particular, even when conventional alcohol compounds can not be used as raw materials or intermediates, the alcohol compound of the present invention can be used as a raw material or an intermediate therefor to make it possible to produce various paints, adhesives, medicines, cosmetics, food additives, surfactants and the like, and the technique can be enriched.

The invention claimed is:
1. An alcohol compound represented by Formula (2):

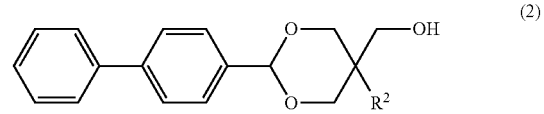

(2)

wherein $R^2$ represents a hydrogen atom, methyl or ethyl.

2. An alcohol compound represented by Formula (4):

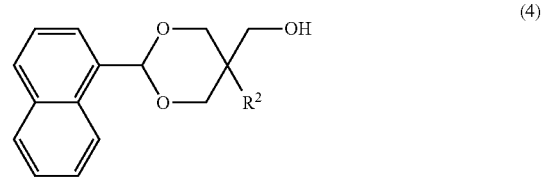

(4)

wherein $R^2$ represents a hydrogen atom, methyl or ethyl.

3. The alcohol compound according to claim 1, wherein $R^2$ is a hydrogen atom.

4. The alcohol compound according to claim 1, wherein $R^2$ is methyl.

5. The alcohol compound according to claim 1, wherein $R^2$ is ethyl.

6. The alcohol compound according to claim 2, wherein $R^2$ is a hydrogen atom.

7. The alcohol compound according to claim 2, wherein $R^2$ is methyl.

8. The alcohol compound according to claim 2, wherein $R^2$ is ethyl.

* * * * *